United States Patent [19]

Wachs et al.

[11] Patent Number: 4,544,649

[45] Date of Patent: Oct. 1, 1985

[54] CATALYSTS COMPRISING TANTALA SUPPORTED ON TITANIA

[75] Inventors: Israel Wachs, Bridgewater; Claudio C. Chersich, Englewood Cliffs, both of N.J.

[73] Assignee: Exxon Research and Engineering Co., Florham Park, N.J.

[21] Appl. No.: 626,066

[22] Filed: Jun. 29, 1984

[51] Int. Cl.[4] .......................... B01J 21/06; B01J 23/20
[52] U.S. Cl. .................................................... 502/350
[58] Field of Search ................................ 502/350, 353

[56] References Cited

U.S. PATENT DOCUMENTS 4,233,139  11/1980  Murrell et al. .................. 502/350 X
4,467,047  8/1984  Johnson .......................... 502/353 X Primary Examiner—W. J. Shine
Attorney, Agent, or Firm—Edward M. Corcoran

[57] ABSTRACT

Catalysts comprising an oxide of tantalum supported on titania wherein at least a portion, and preferably at least about 25 wt. %, of said supported tantalum oxide is in a non-crystalline form. These catalysts have been found to be useful for synthesizing methanethiol and $CH_4$ from mixtures of $H_2S$ and CO.

5 Claims, No Drawings

CATALYSTS COMPRISING TANTALA SUPPORTED ON TITANIA

BACKGROUND OF THE INVENTION

Field of the Invention

This invention relates to a catalyst composition of matter comprising an oxide of tantalum supported on a titania support wherein at least a portion of the supported tantalum oxide is in a non-crystalline form.

BACKGROUND OF THE DISCLOSURE

U.S. Pat. No. 4,149,998 to Tauster et al. relates to heterogeneous catalysts consisting of Group VIII metals, dispersed on oxide carriers selected from the group consisting of Ti, V, Nb, Ta and mixtures thereof and zirconium titanate and $BaTiO_3$. However, there is no suggestion in this patent that the niobium, vanadium or tantalum be supported on titania.

SUMMARY OF THE INVENTION

The present invention relates to catalyst compositions comprising an oxide of tantalum supported on titania wherein at least a portion of said supported tantalum oxide is in a non-crystalline form. These catalyst compositions are useful for synthesizing methanethiol, $CH_3SH$ and $CH_4$ from mixtures of $H_2S$ and CO. The compositions of this invention are also useful as catalyst supports for supporting iron carbide or ruthenium for Fischer-Tropsch hydrocarbon synthesis reactions. In a preferred embodiment at least about 25 wt.% of the supported tantalum oxide will be in a noncrystalline form.

DETAILED DESCRIPTION

As previously stated, the catalyst compositions of the present invention comprise an oxide of tantalum supported titania wherein at least a portion of the supported tantalum oxide, and preferably at least about 25 wt.% thereof is in a non-crystalline form.

In the catalyst composition of this invention the surface of the titania is modified by the tantalum oxide in an amount such that the modified surface of the so-modified titania exhibits properties different from titania whose surface has not been modified and also different from bulk tantalum oxides. Consequently, the catalyst compositions exhibit properties different from both unmodified titania and bulk oxides tantalum.

Thus, the catalysts of this invention comprise titania whose surface has been modified with an oxide of tantalum. That is, the surface of the titania has been modified by the supported tantalum oxide in an amount such that the catalyst exhibits properties different from titania whose surface has not been modified and different from bulk oxides of and tantalum. Those skilled in the art know that tantalum oxides are crystalline in their bulk form. Thus, at least a portion of and preferably at least about 25 wt.% of the supported tantalum oxide will be in a non-crystalline form. This will be accomplished if the tantalum oxide loading on the titania broadly ranges between about 0.5 to 25 wt.% of the total catalyst weight.

In preparing the catalyst compositions of this invention an oxide or precursor thereof of a tantalum is deposited on the titania to form either the surface modified titania catalyst composition of this invention or, in the case of one or more tantalum oxide precursors, a catalyst precursor composite. The precursor composite is then calcined to oxidize the precursor composite to form a catalyst composition of this invention. The catalyst precursor composites of this invention may be prepared by techniques well-known in the art, such as incipient wetness, impregnation, etc., the choice being left to the practitioner. When using the impregnation technique, the impregnating solution is contacted with the support material for a time sufficient to deposit the precursor material onto the support either by selective adsorption or alternatively, the excess solvent may be evaporated during drying leaving behind the precursor salt. Advantageously, incipient wetness techniques may also be used. The choice of catalyst preparation is left to the practitioner. The tantalum oxide precursor salt solution used in preparing the catalyst of this invention may be aqueous or organic, the only requirement being that an adequate amount of precursor compound for the tantalum metal oxide be soluble in the solvent used in preparing this solution.

The final catalyst composite will then normally be dried at temperatures ranging from about 50°–300° C. to remove the excess solvent and, if necessary decompose the salt if it is an organic salt. The tantalum oxide precursor is then converted into the oxide form by calcining at temperatures of from about 150° to 800° C. and preferably 300°–700° C. in a suitable oxidizing atmosphere such as air, oxygen, etc. The time required to calcine the composite will, of course, depend on the temperature and in general will range from about 0.5 to 7 hours. Reducing atmospheres may also be used to decompose the tantalum metal oxide precursor, but the resulting composite will then require subsequent calcination to convert the reduced metal component to the oxide form.

The catalysts of this invention will generally have tantalum oxide loadings of from about 0.5 to 25 wt.% metal oxide based on the total catalyst composition, preferably from about 1 to 15 wt.%, more preferably from about 2–10 wt.% based on the total catalyst composition.

The invention will be more readily understood by reference to the following example.

EXAMPLE

EXAMPLE 1

Experimental

Hydrogen sulfide was obtained in compressed cylinders from Scientific Gas Products (electronic grade 99.999% purity), while carbon monoxide was purchased from Matheson Gas (99.99% purity). The above gases were checked for absence of hydrocarbon impurities (MS analysis and G.C. analysis with FID detector) and used without further purification. Helium (99.99%), when used as an inert carrier gas, was predried in a molecular sieve trap, scrubbed for $O_2$ removal in a hot Cu trap, and redried in a molecular sieve trap. Gas flows were regulated with Tylan F-260 flow controllers and premixed in a gas manifold system prior to entering into the catalyst bed.

A quartz reactor tube of 9 mm ID by 700 mm was loaded with 2.5 gram samples of −40/+60 mesh (Tyler) catalyst particles which were supported on each end with degreased quartz wool plugs. An external thermocouple was attached to the outside of the quartz tube near the center of the catalyst bed to record reaction temperature. The tube was heated with a three zone electric furnace (ATS-3210) equipped with Omega set point controllers.

Product analysis was accomplished with an on-line Carle GC (series SX) equipped with a hydrogen transfer system and FID/TC detectors. Gas phase samples were also separated on a Perkin Elmer 900 GC coupled to a DuPont 21-491 mass spectrometer for product identification of $CH_3SH$ and $CH_3SCH_3$. Response factors for quantitative G.C. analysis were obtained from a primary standard mixture of gases with quantities similar to the product mixture.

Catalyst Preparation

Degussa P-25, a mixture of anatase and rutile titania, was used as the titania support. The catalyst was prepared in a glove box in a nitrogen atmosphere to prevent decomposition of the tantalum oxide precursor. Ten grams of the P-25 titania powder were slurried in 100 cc of ethanol to which was added the tantalum oxide precursor, with the resulting mixture stirred overnight, under flowing nitrogen, to evaporate the ethanol. The dry mixture was then taken out of the glove box and 3 cc of water added. The resulting mixture was stirred overnight in air, then the dry powder placed in a quartz boat and slowly heated in a 1/1 flowing mixture of $O_2$ in He up to 400° C. At 400° C. the He flow was cut off and the powdered catalyst precursor then heated from 400° to 575° C. in 100% $O_2$. The sample of catalyst precursor was held at 575° C. in the $O_2$ for two hours to calcine the precursor into a catalyst of this invention.

The transition metal oxide precursor was obtained from Alfa, Inc. and was $Ta(C_2H_5O)_5$. The amount of tantala precursors added to the slurry of 10 g P-25 in 100 cc of ethanol was 1.84 grams. The resulting catalyst contained 10 wt.% tantala on titania. The tantala content of the catalyst is expressed as tantalum pentoxide.

In this experiment a 2 gram sample of the catalyst was charged to the reactor which was then heated up to a temperature of 200° C. in flowing helium. After the reactor achieved a temperature of 200° C., a 1/1 molar mixture of $H_2S/CO$ feed at a flow rate of about 4 cc/min. was introduced to the reactor. The reactor was then held at isothermal conditions in order to establish steady-state conditions with respect to feed conversion and product selectivity. The temperaure was then raised at 50° C. intervals and held at each temperature for one hour to measure activity and selectivity. The final temperature reached was 400° C. The reactor was then cooled to 300° C. to recheck the activity compared to the activity during the heating step.

The results are shown in the Table and clearly demonstrate that the catalyst was effective for the conversion of the $H_2S/CO$ feed.

| \multicolumn{2}{c}{$H_2S$ AND CO CONVERSION AS A FUNCTION OF TEMPERATURE[a]} | |
| --- | --- |
| Catalyst | 10% $Ta_2O_5/TiO_2$ |
| Surface Area[b] | 54 $m^2/g$ |
| Catalyst Weight | 2.0 g |
| CO Conversion (%) | |
| 300° C. | 9% |
| 300° C. | 19% |
| 350° C. | 33% |
| 400° C. | 33% |
| $H_2S$ Conversion (%) | |
| 300° C. | 2.5 |
| 300° C. | 8 |
| 350° C. | 16 |
| 400° C. | 18 |

Notes:
[a]Products included $CH_3SH$ and $CH_4$
[b]BET
[c]After cooling from 400° C.

What is claimed is:

1. A catalyst composition comprising an oxide of tantalum supported on titania wherein at least a portion of the supported tantalum metal oxide is in a non-crystalline form.

2. The catalyst of claim 1 wherein at least about 25 wt.% of said supported tantalum oxide is in a non-crystalline form.

3. The catalyst of claim 2 wherein the amount of supported tantalum oxide present on said catalyst ranges from about 0.5 to 25 wt.% of the catalyst composition.

4. The catalyst of claim 3 wherein the amount of supported tantalum oxide ranges from about 1 to 15 wt.% of the catalyst composition.

5. The catalyst of claim 4 wherein the amount of supported tantalum oxide ranges from about 2 to 10 wt.% of the catalyst composition.

* * * * *